United States Patent
Prien

(10) Patent No.: US 9,724,108 B2
(45) Date of Patent: Aug. 8, 2017

(54) SLEEVE CLAMP

(71) Applicant: Stryker Trauma GmbH, Schönkirchen (DE)

(72) Inventor: Ole Prien, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 560 days.

(21) Appl. No.: 14/296,972

(22) Filed: Jun. 5, 2014

(65) Prior Publication Data

US 2014/0364863 A1    Dec. 11, 2014

(30) Foreign Application Priority Data

Jun. 7, 2013   (EP) .................................... 13171062

(51) Int. Cl.
*A61B 17/17* (2006.01)
*A61B 17/34* (2006.01)
*A61B 17/00* (2006.01)

(52) U.S. Cl.
CPC .......... *A61B 17/17* (2013.01); *A61B 17/1728* (2013.01); *A61B 2017/00469* (2013.01); *A61B 2017/347* (2013.01); *A61B 2017/3492* (2013.01)

(58) Field of Classification Search
CPC ............ A61B 17/1725; A61B 17/1717; A61B 2017/3407; A61B 17/3421; A61B 17/175; A61B 17/1753
See application file for complete search history.

(56) References Cited

U.S. PATENT DOCUMENTS

| | | | |
|---|---|---|---|
| 4,710,075 A * | 12/1987 | Davison | A61B 17/16 33/512 |
| 4,920,958 A * | 5/1990 | Walt | A61B 17/1714 606/103 |
| 5,480,389 A | 1/1996 | McWha et al. | |
| 6,039,739 A | 3/2000 | Simon | |
| 7,311,710 B2 | 12/2007 | Zander | |
| 7,549,994 B2 | 6/2009 | Zander et al. | |
| 2009/0216242 A1 | 8/2009 | Riemer et al. | |

FOREIGN PATENT DOCUMENTS

DE      102009018641 A1   10/2010
EP         2548523 A1    1/2013

OTHER PUBLICATIONS

Japanese Office Action for Application No. 2014-116462 dated Apr. 14, 2015.
European Search Report of Application No. EP13171062 dated Oct. 21, 2013.

* cited by examiner

*Primary Examiner* — Andrew Yang
(74) *Attorney, Agent, or Firm* — Lerner, David, Littenberg, Krumholz & Mentlik, LLP

(57) ABSTRACT

A sleeve clamp has a body with a through bore for receiving a sleeve, and a clamping element. The clamping element includes a clamping edge and may be arranged at the body so as to be movable between two positions, i.e. a neutral position and a deflected position. In the neural position, the clamping edge protrudes laterally into a lumen which is occupied by the sleeve when the sleeve is received in the through bore. In the deflected position, the clamping element may be elastically deformed and the clamping edge does not protrude into the lumen which is occupied by the sleeve when the sleeve is received in the through bore.

23 Claims, 3 Drawing Sheets ated with the text by reference.

SLEEVE CLAMP

CROSS-REFERENCE TO RELATED APPLICATIONS

The present application claims priority to European Patent Application No. 13 171 062.6 filed Jun. 7, 2013, of which is hereby incorporated herein by reference.

BACKGROUND OF THE INVENTION

The invention relates to a device for holding a sleeve. In particular, the invention relates to a sleeve clamp. A sleeve may be utilized for leading, for example, a screw along a predetermined path. In particular, a tissue protection sleeve may be utilized to hold soft tissue aside when inserting a bone screw into a bone, for example so as to fix a fracture of the bone.

Previous to the insertion of a screw, the sleeve may facilitate an insertion of an instrument like a drill for drilling a bore, or a measuring instrument for determining an appropriate length of a screw to be inserted.

However, the sleeve may be displaced by soft tissue structures surrounding a bone so that a screw insertion may be affected.

U.S. Patent Publication No. 2009/0216242 describes a clamp for a Kirschner wire. A Kirschner wire received in a sleeve is laterally pressed against an edge of the sleeve so as to hold the Kirschner wire in place. However, the Kirschner wire will tilt in the sleeve, i.e. the wire axis will be inclined relative to the sleeve axis.

U.S. Pat. No. 7,549,994 as well as U.S. Pat. No. 6,039,739 disclose a targeting device with a targeting arm, the targeting arm including a solid portion and an elastic portion. The elastic portion is separated from the solid portion by a slit. A through bore for receiving a wire or a sleeve is formed through both the solid portion and the elastic portion. The elastic portion can be used to fix a position of the wire or sleeve when being inserted in the through bore.

U.S. Pat. No. 7,311,710, the disclosure of which is incorporated herein by reference, describes a resiliently deflectable lever which may cooperate with a sleeve which is guided through a transverse bore in a targeting arm portion, in a clamping manner when the lever is in a relaxed or released condition.

BRIEF SUMMARY OF THE INVENTION

An aspect of the invention may be defined as providing a device for easily and firmly holding an elongated element like a wire or a sleeve, without affecting a position and orientation of said element.

This is achieved by the subject-matter of the independent claim. Further embodiments are described in the dependent claims.

In general, a sleeve clamp comprises a body with a through bore for receiving a sleeve, and a clamping element. The clamping element includes a clamping edge and may be arranged at the body so as to be movable between two positions, i.e. a neutral position and a deflected position. In the neural position, the clamping edge protrudes laterally into a lumen which is occupied by the sleeve when the sleeve is received in the through bore. In the deflected position, the clamping element may be elastically deformed and the clamping edge does not protrude into the lumen which is occupied by the sleeve when the sleeve is received in the through bore.

In other words, a clamping element is provided at the body of the sleeve clamp, which clamping element protrudes into a free lumen, for example a through bore, as long as no sleeve is inserted into the lumen. The clamping element will be displaced out of the lumen as soon as a sleeve has been inserted into said lumen.

According to an embodiment, the clamping element may be elastically deformable resulting in a restoring force which may press a clamping edge of the clamping element against the outer surface of the sleeve. Furthermore, a sleeve may be inserted against the restoring force of the clamping element, and pushed through the through bore in the body of the sleeve clamp. The pressing of the clamping edge against the sleeve holds the sleeve in position. The deflection of the clamping element further provides an axial force component which prevents an axial movement of the sleeve, in particular in a direction opposite to the sleeve inserting direction, even against any forces acting on the sleeve.

According to an embodiment, the clamping element may be formed as a leaf spring.

According to another embodiment, the clamping element may extend substantially perpendicular to a longitudinal axis of the through bore in which the sleeve may be received.

It will be appreciated that the clamping element may be a separate element which is attached to the body of the sleeve clamp, for example by means of a screw or pin, by use of an adhesive, or by welding. According to one embodiment, the clamping element may be integrally formed with the body.

So as to achieve a better holding effect, the clamping edge may be curved like a section of an outer circumference of the sleeve. Thus, a line contact of the clamping element at the outer circumferential surface of the sleeve may be achieved.

According to a further embodiment, the sleeve clamp may comprise a push button for manually operating, for example deflecting the clamping element. Thus, the clamping element may be operated so as to release a sleeve or so as to completely open the lumen for receiving a sleeve without hindering forces.

According to an embodiment, the clamping element may be arranged within the body and the body may further comprise an opening in which the push button may be arranged. The push button may also protrude through and out of the opening.

The clamping element may comprise a base portion at which the clamping element is attached to the body, a free end portion including the clamping edge and a middle portion, wherein the push button may be attached to any one of these portions. In particular, the push button may be attached to the middle portion of the clamping element.

As one possibility to attach the push button to the clamping element, the push button may be integrally formed with the clamping element.

According to an embodiment, a top surface of the push button may be substantially at the same level as an outer surface of the body when the clamping element is in the deflected position. It is noted that 'substantially at the same level' should be understood as being substantially in one plane with a certain deviation. For example, the deviation may be in a range up to 30 percent, in particular 15 percent of the path length of the movement of the push button between the neutral position of the clamping element and the deflected position of the clamping element.

According to an embodiment, the opening in the body may be only slightly larger than the width of the push button. In such a case, a finger may come in contact with the outer surface of the body when pressing the push button to the position in which the clamping element is in the deflected position. As it would be difficult to further move the push button and thus the clamping element, an over-deflection of the clamping element may be prevented.

According to an embodiment, the sleeve clamp as described above may be formed as a part of a targeting device for aligning a sleeve for an insertion of a bone screw with a locking hole in a bone nail for receiving the screw.

It has to be noted that a person skilled in the art will gather from the above and the following description that, unless otherwise notified, in addition to any combination of features belonging to one embodiment, also any combination of features relating to another embodiment is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of an exemplary embodiment with reference to the attached drawings.

Figure 1:
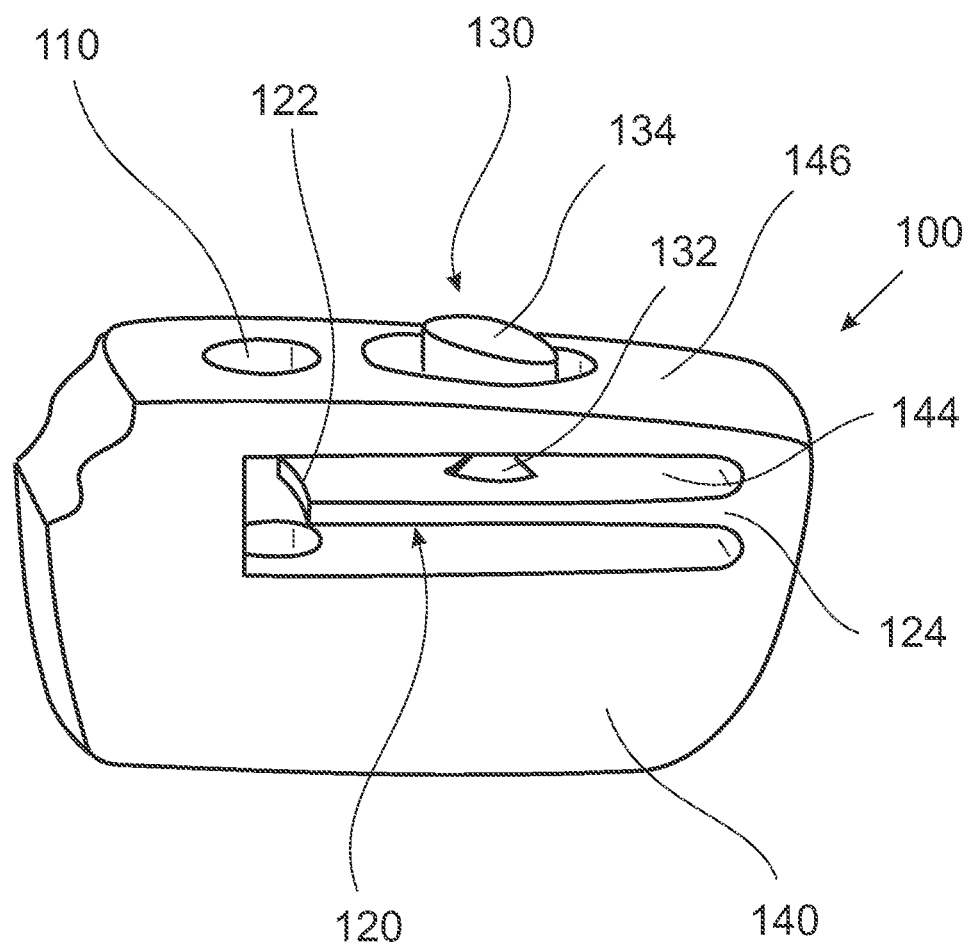
FIG. 1 is an isometric illustration of an embodiment of a sleeve clamp.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION

FIG. 1 is an isometric illustration of an embodiment of a sleeve clamp 100. The sleeve clamp 100 comprises a body 140, a through bore 110, a clamping element 120 and a push button 130.

The clamping element 120 is integrally formed with the body 140, with a transition at a base 124 of the clamping element. Furthermore, the clamping element extends from the base 124 substantially along a plane in a direction to and into the through bore 110, with the front end of the clamping element including a clamping edge 122, protruding into the lumen of the through bore. Here, the clamping element 120 is arranged within a space formed by a lateral recess 144 in body 140, wherein the lateral recess intersects the through bore 110. The clamping element 120 is generally perpendicular to axis 112.

At a middle portion of the clamping element 120, the push button 130 is attached to the clamping element. In particular, the push button is integrally formed with the clamping element, with a base 132 at the clamping element and a top surface 134 protruding out of an opening in the body 140.

Figure 2:
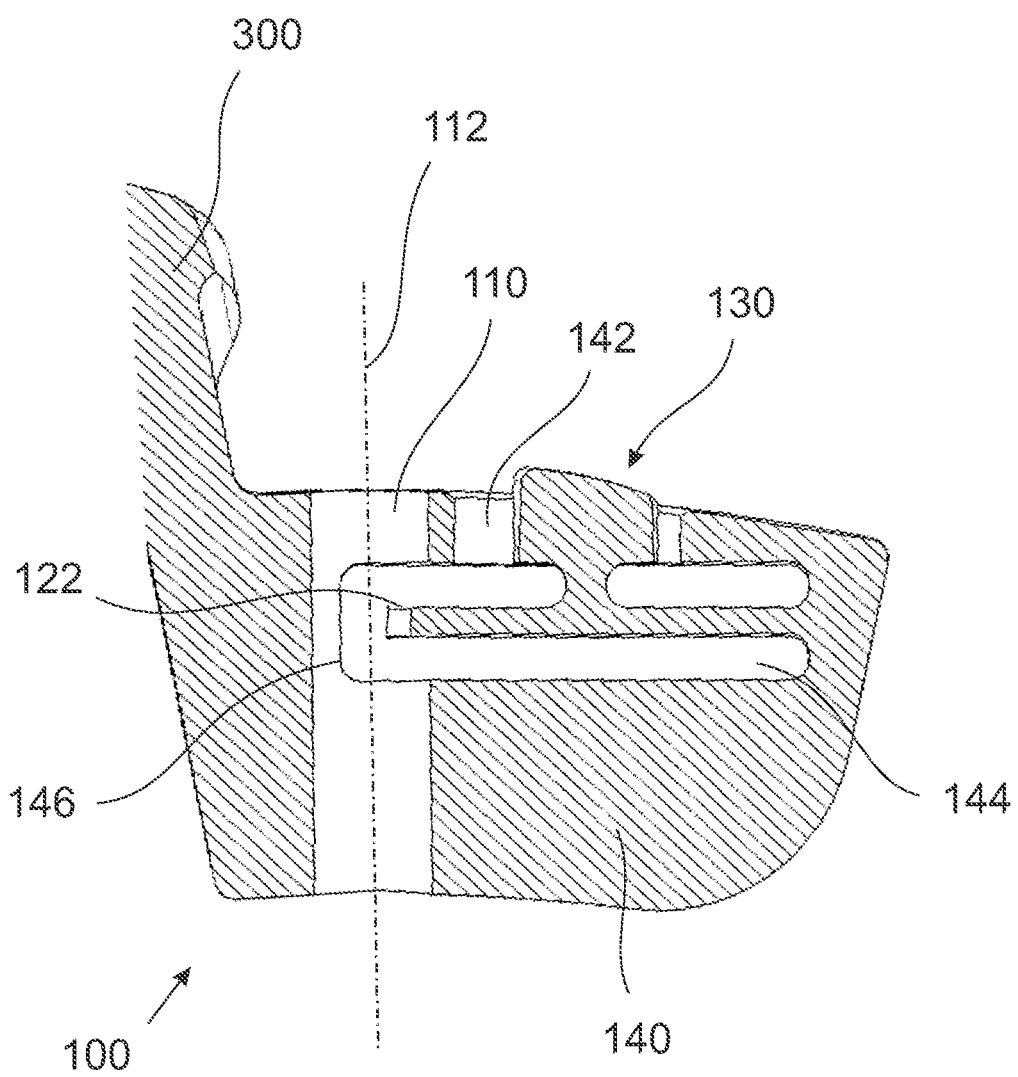
FIG. 2 is a section view of the sleeve clamp of FIG. 1 with the clamping element in a neutral position.

In the section view of FIG. 2, the lateral recess 144, the opening 142 and the position of the clamping edge 122 is shown more clearly. The lateral recess 144 intersects the through bore 110, thus generating visible edges 146 in the surface of the through bore 110. The push button 130 is arranged in the opening 142. The clamping edge 122 protrudes into the lumen of the through bore, i.e. beyond the surface of the through bore 110. Further, a longitudinal axis 112 of the through bore 110 is drawn in so that it can be seen that the clamping element 120 extends substantially perpendicular to this axis 112.

The portion 300 extending away from the body 140 may be a part of a targeting device.

Figure 3:
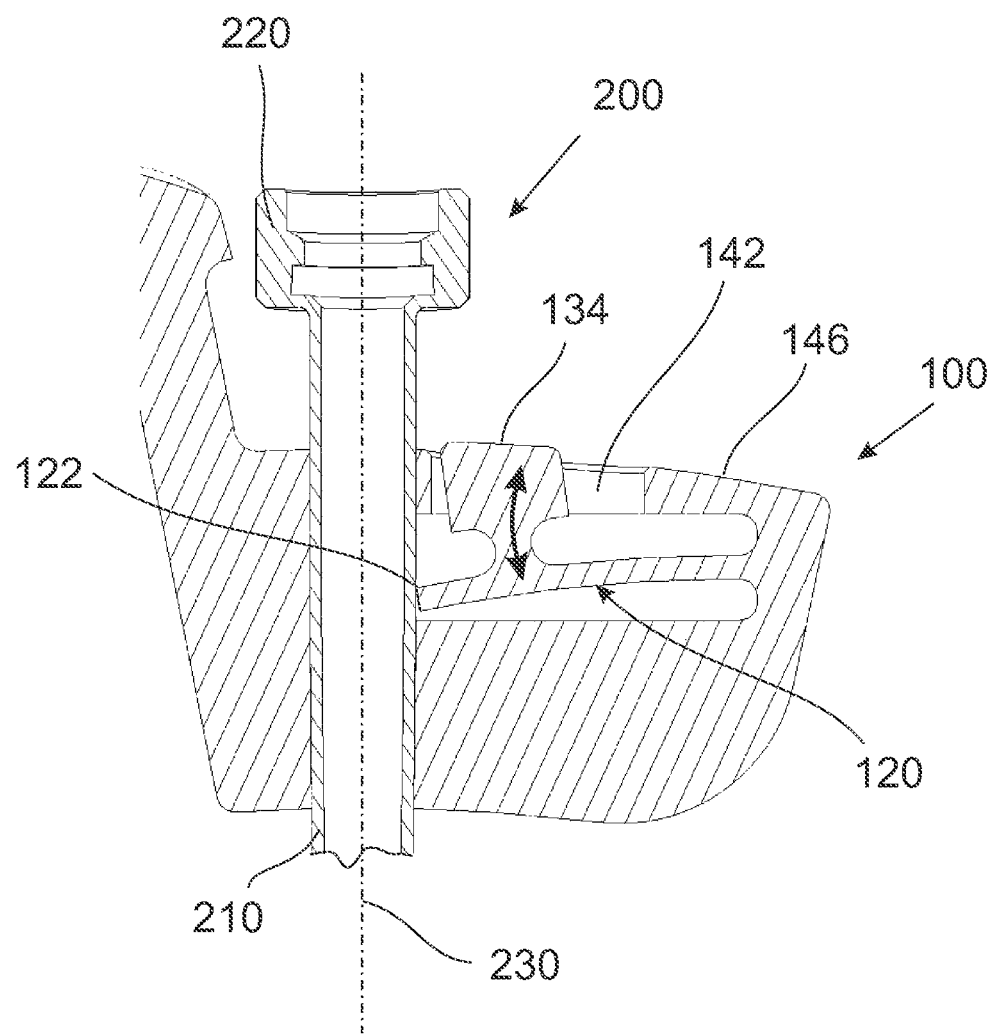
FIG. 3 is a section view of the sleeve clamp of FIG. 1 together with a sleeve, with the clamping element in a deflected position.

While the clamping element 120 is in the neutral position shown in FIGS. 1 and 2, the clamping element 120 is in a deflected position shown in FIG. 3.

In FIG. 3, a sleeve 200 is inserted into the through bore of the sleeve clamp 100. A shaft 210 of the sleeve 200 has a diameter which fits to a diameter of the trough bore so that any lateral movement or tilting of the sleeve within the through bore of the sleeve clamp can be prevented, i.e. the longitudinal axis 230 of the sleeve is congruent or coaxial with the axis 112 of the through bore. When inserting the sleeve 200 into the through bore, starting with the front end (not shown) of the sleeve shaft 210, the front end of the sleeve shaft comes firstly in contact with the end of the clamping element 120 including the clamping edge 122 and then presses the same out of the lumen of the through bore by deflecting the clamping element. When the clamping element 120 is deflected it develops a spring force acting towards the lumen of the through bore 110. This force causes edge 122 of clamping element 120 to engage the outer surface of sleeve 200 and automatically hold it in place in bore 110.

With the clamping element in the deflected position, the top surface 134 of the push button 130 is substantially at or slightly above the level of the outer surface 146 of the body surrounding the opening 142.

The double-arrow in FIG. 3 indicates the deflection movement of the clamping element 120, which movement is substantially parallel to the axis 230 of the sleeve, i.e. the deflection movement is in a plane together with the sleeve axis 230. By further deflecting the clamping element 120 by further depressing push button 130, the clamping edge 122 comes out of contact with the sleeve shaft 210 so that the sleeve is released and may be pulled back and out of through bore. Once sleeve 200 has been removed, push button 130 is released allowing clamping element 120 to return to its neutral position.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practising the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A sleeve clamp comprising:
  a body with a through bore for receiving a sleeve;
  a clamping element having a clamping edge;
  wherein the clamping element is arranged at the body so as to be movable between a neutral position in which the clamping edge protrudes laterally into a lumen which is occupied by the sleeve when the sleeve is received in the through bore, and a deflected position in which the clamping element is elastically deformed and in which the clamping edge does not protrude into the lumen;
  further comprising a push button for manually deflecting the clamping element; and
  wherein the clamping element comprises a base portion at which the clamping element is attached to the body, a free end portion including the clamping edge and a middle portion, wherein the push button is attached to the middle portion of the clamping element.

2. The sleeve clamp of claim 1, wherein the clamping element is formed as a leaf spring.

3. The sleeve clamp of claim 1, wherein the through bore includes a longitudinal axis and wherein the clamping element extends substantially perpendicular to the axis of the through bore.

4. The sleeve clamp of claim 1, wherein the clamping element is integrally formed with the body.

5. The sleeve clamp of claim 1, wherein the clamping edge is curved so as to fit to a section of a curved outer circumference of the sleeve.

6. The sleeve clamp of claim 1, wherein the clamping element is arranged in the body and the body further comprises an opening, wherein the push button is arranged in the opening.

7. The sleeve clamp of claim 6, wherein the push button protrudes through and out of the opening.

8. The sleeve clamp of claim 1, wherein the push button is integrally formed with the clamping element.

9. The sleeve clamp of claim 1, wherein the push button includes a top surface and the body includes an outer surface surrounding the opening, and wherein the top surface of the push button is substantially at the same level as the outer surface of the body when the clamping element is in the deflected position.

10. The sleeve clamp of claim 1, wherein the sleeve clamp is formed as a part of a targeting device for aligning a sleeve for an insertion of a bone screw into a locking hole in a bone nail receiving the screw.

11. A targeting device for a bone nail comprising:
  a connecting portion connectable to an end of the nail and having a targeting arm with a first portion extending parallel to the bone nail when the bone nail is connected to the connecting portion, the first portion is provided with a sleeve clamp comprising;
  a body with a through bore for receiving a guiding sleeve;
  a clamping spring element having a clamping edge;
  wherein the clamping spring element is arranged at the body so as to be movable between a deflected position and a neutral position in which the clamping edge protrudes laterally into a lumen which is occupied by the guiding sleeve when the guiding sleeve is received in the through bore, wherein when the clamping spring element is in the deflected position the clamping spring element is elastically deformed and the clamping edge does not protrude into the lumen; and
  the targeting device further comprising a push button for manually deflecting the clamping spring element.

12. The targeting device of claim 11, wherein the clamping element is formed as a leaf spring.

13. The targeting device of claim 11, wherein the through bore includes a longitudinal axis and wherein the clamping spring element extends substantially perpendicular to the axis of the through bore.

14. The targeting device of claim 11, wherein the clamping spring element is integrally formed with the sleeve clamp body.

15. The targeting device of claim 11, wherein the guiding sleeve has a cylindrical outer surface and the spring element clamping edge is curved so as to fit to a section of an outer circumference of the guiding sleeve.

16. The targeting device of claim 11, wherein the clamping spring element is arranged in the body and the body further comprises an opening, wherein the push button is arranged in the opening and has a top portion adjacent an outer surface of the body.

17. The targeting device of claim 16, wherein the clamping spring element comprises a base portion at which the clamping spring element is attached to the body, a free end portion including the clamping edge and a middle portion, wherein the push button is attached to the middle portion of the clamping element.

18. The targeting device of claim 17, wherein the push button is integrally formed with the clamping spring element.

19. The targeting device of claim 17, wherein the push button includes a top surface and the body includes an outer surface surrounding the opening therein and wherein the top surface of the push button is substantially at the same level as the outer surface of the body when the clamping spring element is in the deflected position.

20. The targeting device of claim 17, wherein the sleeve clamp body and targeting arm are formed as one-piece and the lumen is for aligning the sleeve for an insertion of a bone screw into locking hole in the bone nail.

21. A sleeve clamp comprising:
  a body with a through bore for receiving a sleeve, and
  a longitudinally extending clamping element extending between a base and a clamping edge,
  wherein the clamping element base is fixedly coupled to the body so that the clamping edge is movable between a neutral position in which the clamping edge protrudes laterally into a lumen which is occupied by the sleeve when the sleeve is received in the through bore, and a deflected position in which the clamping element is elastically deformed about the base and in which the clamping edge does not protrude into the lumen; and
  wherein the clamping element is mounted within a cavity in the body and the longitudinal axis thereof in the neutral position extends in a direction substantially perpendicular to the longitudinal axis of the through bore.

22. The sleeve clamp of claim 21, wherein the clamping element is integrally formed with the body.

23. The sleeve clamp of claim 21, further comprising a push button for manually deflecting the clamping element out of the neutral position.

* * * * *